United States Patent [19]
Badger et al.

[11] Patent Number: 5,981,538
[45] Date of Patent: Nov. 9, 1999

[54] METHODS OF TREATING PSORIASIS EMPLOYING SUBSTITUTED AZASPIRANES

[75] Inventors: Alison Mary Badger, Bryn Mawr; Don Edgar Griswold, North Wales, both of Pa.

[73] Assignee: AnorMED Inc., Langley, Canada

[21] Appl. No.: 08/792,691

[22] Filed: Jan. 29, 1997

Related U.S. Application Data

[63] Continuation of application No. 08/382,031, filed as application No. PCT/US93/07632, Aug. 12, 1993.

[30] Foreign Application Priority Data

Aug. 13, 1992 [GB] United Kingdom .................. 9217116

[51] Int. Cl.$^6$ ....................................................... A61K 31/44
[52] U.S. Cl. ........................................... 514/278; 514/863
[58] Field of Search ..................................... 514/278, 863

[56] References Cited

U.S. PATENT DOCUMENTS 4,963,557  10/1990  Badger et al. ........................... 514/278
5,064,835  11/1991  Bochis et al. ........................... 514/291

*Primary Examiner*—Kevin E. Weddington
*Attorney, Agent, or Firm*—Morrison & Foerster LLP

[57] ABSTRACT

Invented is a method of treatment of psoriasis in a mammal in need thereof which comprises administering to such mammal an effective amount of a substituted azaspirane.

10 Claims, No Drawings

METHODS OF TREATING PSORIASIS EMPLOYING SUBSTITUTED AZASPIRANES

This is a continuation of application Ser. No. 08/382,031, filed Feb. 10, 1995, now abandoned, which is a 371 of PCT/US93/07632 filed Aug. 12, 1993.

METHODS

This invention relates to a method of treatment of psoriasis in a mammal in need thereof which comprises administering to such mammal an effective amount of a substituted azaspirane.

BACKGROUND OF THE INVENTION

Badger et al., U.S. Pat. No. 4,963,557 (Badger I) discloses compounds of the formula

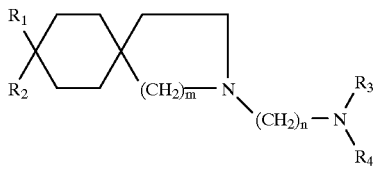

(I)

wherein: n is 3–7; m is 1 or 2; $R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms; $R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms; or a pharmaceutically acceptable salt or hydrate or solvate thereof.

Badger I does not disclose or claim the compounds of Formula I for the treatment of psoriasis.

SUMMARY OF THE INVENTION

This invention relates to a method of treatment of psoriasis in a mammal in need thereof which comprises administering to such mammal an effective amount of a compound of the formula

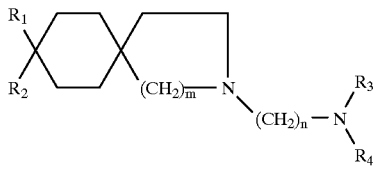

(I)

wherein:
n is 3–7;
m is 1 or 2;
$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;
$R^3$ and $R^4$ are the same or different and are selected from hydrogen or straight chain alkyl having 1–3 carbon atoms; or $R^3$ and $R^4$ are joined together with the nitrogen atom to form a heterocyclic group having 5–8 atoms; or a pharmaceutically acceptable salt or hydrate or solvate thereof.

DETAILED DESCRIPTION OF THE INVENTION

The term "treatment" as used in the specification and in the claims is meant that a mammal in need of antipsoriatic activity is cured of or provided with acceptable symtomatic relief from the disease.

The term "effective amount" as used herein is meant the amount needed to effect treatment as defiend above.

The term "mammal" as used herein is meant warmed-blooded vertebrate animals, including all that possess hair and suckle their young. Preferably, said mammal is a human.

The preparation of all compounds of Formula (I) (active ingredient) and pharmaceutically acceptable salts, hydrates and solvates and formulations thereof is discolsed in U.S. Pat. No. 4,963,557, the entire disclosure of which is hereby incorporated by reference.

As used herein, the term "compound A" refers to the dihydrochloride salt of a compound of Formula (I) where $R^1$ and $R^2$ are propyl, $R^3$ and $R^4$ are joined together with the nitrogen to form a piperidine ring, m is 1 and n is 3 which is 8,8-dipropyl-2-azaspiro[4.5]decane-2-piperidinopropyl dihydrochloride.

Histologically, psoriasis is characterized by epidermal thickening, with an overlying scale, epidermal neutrophilic infiltrates, and dilated dermal capillaries (Phillips, et al. *N. Engl J. Med.* 326 No.3, (Jan. 16, 1992) 167–177) as well as abnormally increased epidermal cell proliferation(epidermal hyperplasia) (*Drug & Market Development* 2, No 9/10, (Jan. 31, 1992) 146–149). Particularly characteristic of the disease state of psoriasis is epidermal neutrophlic infiltration.

It has now been discovered that compounds of Formula (I) and pharmaceutically acceptable salts or hydrates or solvates thereof are useful for treatment of psoriasis in a mammal in need of such treatment.

Preferred compounds for use in the presently invented methods are: N,N-dimethyl-8,8-dipropyl-2-azaspiro[4.5] decane-2-propanamine and 8,8-dipropyl-2-azaspiro[4.5] decane-2-piperidinopropyl.

Compound A was tested for its in vivo ability to inhibit cutaneous inflammation in the 12-0-tetradecanoylphorbol acetate (TPA) induced ear edema test (Young, et al., *J. Invest. Derm.,* 80:40–52, 1983), with subsequent analysis of myeloperoxidase activity (indicating the degree of neutrophil infiltration (Bradley et al. *J. Invest. Derm.,* 78 206–209, 1982.)) in the subject ear.

To perform the experiments male Balb/c inbred mice (Charles River Breeding Laboratories, Kingston, N.Y.) were used. Within a single experiment mice (22–25 g) were age matched. The in vivo experiments involved use of 5–6 animals/treatment group and a control group of 6–10 animals. TPA. (Sigma Chemical Company) in acetone (4 µg/20 µl) was applied to the inner and outer surfaces of the left ear of the Balb/c male mice. Compound A was suspended in ethanol or methanol and applied topically to the left ear of test animals 5 minutes after TPA administration. The thickness of both ears was measured with a dial micrometer (Mitutoyo, Japan) at specified times post treatment and the data expressed as the change in thickness between treated and untreated ears. The application of acetone does not cause an edematous response; therefore, the difference in ear thickness represents a response to TPA. After measuring the edema, the treated left ears were removed and stored at −70° C. until they were assayed for myeloperoxidase (MPO) activity.

In order to determine MPO activity the above described treated left ear tissues were partially thawed, minced and then homogenized (10% w/v) with a Tissumized homogenizer (Tekmar Co) in 50 mM phosphate buffer (pH 6) containing 0.5% HTAB. The tissue homogenates were taken through three cycles of freeze-thaw, followed by brief sonication (10 sec). The method of Bradly et al. (referenced above) was used with modifications as described. The appearance of a colored product from the MPO-dependent reaction of o-dianisidine (0.167 mg/ml; Sigma) and hydrogen peroxide (0.0005%:Sigma) was measured spectrophotometrically at 460 nm. Supernatant MPO activity was quantified kinetically (change in absorbance measured over 3 minutes, samples at 15 second intervals) using a Beckman DU-7 spectrophotometer and a Kinetics Analysis package (Beckman Instruments, Inc.). One unit of MPO activity is defined as that degrading one micromole of peroxide per minute at 25° C.

Mice treated with Compound A experienced significant inhibition of edematogenic response and neutrophil infiltration, to TPA. Thus, the administration of a compound of Formula I results in a therapeutic treatment of psoriasis in mammals.

This invention relates to a method of treatment of psoriasis in a mammal in need of such treatment which comprises administering an effective amount of a compound of Formula (I) or a pharmaceutically acceptable salt or hydrate or solvate thereof. A compound of Formula (I) or a pharmaceutically acceptable salt or hydrate or solvate thereof can be administered to such mammal in a conventional dosage form prepared by combining a compound of Formula (I) or a pharmaceutically acceptable salt or hydrate or solvate thereof, with a conventional pharmaceutically acceptable carrier or diluent according to known techniques, such as those described in Badger (I), U.S. Pat. No. 4,963, 557.

It will be recognized by one of skill in the art that the form and character of the pharmaceutically acceptable carrier or diluent is dictated by the amount of active ingredient with which it is to be combined, the route of administration and other well-known variables. A compound of Formula (I) or a pharmaceutically acceptable salt or hydrate or solvate thereof is administered to a mammal in need of antipsoriatic activity in an amount sufficient to cure or to provide acceptable symtomatic relief from the disease.

The route of administration of the Formula (I) compound is not critical but is usually oral or parenteral or topical, preferably topical. The present invention is thus also concerned with providing suitable topical and systemic pharmaceutical formulations for use in the novel methods of treatment of the present invention. The term parenteral as used herein includes intravenous, intramuscular, subcutaneous, intranasal, intrarectal, transdermal, intravaginal or intraperitoneal administration. The subcutaneous and intramuscular forms of parenteral administration are generally preferred. The daily parenteral dosage regimen will preferably be from about 0.01 mg/kg to about 10 mg/kg of total body weight, most preferably from about 0.1 mg/kg to about 1 mg/kg. The daily oral dosage regimen will preferably be from about 0.01 mg/kg to about 10 mg/kg of total body weight. The daily topical dosage regimen will preferably be from aobut 0.01 mg/kg to about 10 mg/kg.

Preferably, each parenteral dosage unit will contain the active ingredient in an amount of from about 0.1 mg to about 100 mg. Preferably each oral dosage unit will contain the active ingredient in an amount of from about 0.1 mg to about 100 mg. Preferably each topical dosage unit will contain the active ingredient in an amount of from about 0.1 mg to about 100 mg.

The compounds of Formula (I) which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavoring or coloring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

The compounds of the present invention are also administered in the form of a pharmaceutical composition comprising the active ingredient in combination with a pharmacologically acceptable carrier adapted for topical administration. These topical pharmaceutical compositions may be in the form of a solution, cream, ointment, gel, lotion, shampoo or aerosol formulation adapted for application to the skin. These topical pharmaceutical compositions containing the compounds of the present invention ordinarily include above 0.1% to 15%, preferably about 0.1 to 5%, and more preferably about 0.1% to 2%, of the active compound, in a mixture with a pharmaceutically acceptable carrier.

While it is possible for an active ingredient to be administered alone, it is preferable to present it as a pharmaceutical formulation.

It will be recognized by one skill in the art that the optimal quantity and spacing of individual dosages of a compound of formula (I) or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt or hydrate or solvate thereof given per day and duration of therapy, can be ascertained by those skilled in the art using conventional course of treatment determination tests.

In addition, the compounds of the present invention can be co-administered with further active ingredients, or therapies known for the treatment of psoriasis such as; keratinolytics, topical corticosteroids, coal tar and ultraviolet light or cyclosporine A.

Without further elaboration, it is believed that one skilled in the art can, using the preceding description, utilize the present invention to its fullest extent. The following examples are, therefore, to be construed as merely illustrative and not a limitation of the scope of the present invention in any way.

EXAMPLE 1

Capsule Composition

An oral dosage form for administering Formula (I) compounds is produced by filling a standard two piece hard gelatin capsule with the ingredients in the proportions shown in Table I, below.

TABLE I

| INGREDIENTS | AMOUNTS |
| --- | --- |
| 8,8-dipropyl-2-azaspiro[4.5]decane-2-piperidinopropyl dihydrochloride | 25 mg |
| Lactose | 55 mg |
| Talc | 16 mg |
| Magnesium Stearate | 4 mg |

EXAMPLE 2

Injectable Parenteral Composition

An injectable form for administering Formula (I) compounds is produced by stirring 1.5% by weight of 8,8-dipropyl-2-azaspiro[4.5]decane-2-piperidinopropyl dihydrochloride in 10% by volume propylene glycol in water.

EXAMPLE 3

Tablet Composition

The sucrose, calcium sulfate dihydrate and Formula (I) compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 8,8-dipropyl-2-azaspiro[4.5]decane-2-piperidinopropyl dihydrochloride | 20 mg |
| calcium sulfate dihydrate | 30 mg |
| sucrose | 4.0 mg |
| starch | 2.0 mg |
| talc | 1.0 mg |
| stearic acid | 0.5 mg |

EXAMPLE 4

Alcoholic Solution

| INGREDIENTS | AMOUNTS |
| --- | --- |
| 8,8-dipropyl-2-azaspiro[4.5]decane-2-piperidinopropyl dihydrochloride | 15.0% by weight |
| Water | 45 |
| Ethyl Alcohol | 40 |

EXAMPLE 5

Topical Cleanser

| INGREDIENTS | AMOUNTS |
| --- | --- |
| 8,8-dipropyl-2-azaspiro[4.5]decane-2-piperidinopropyl dihydrochloride | 10.0% by weight |
| Water | 70.439 |
| Chamomile | 0.01 |
| Aloe vera gel | 0.01 |
| Allantoin | 0.001 |
| Triethanolomine | 0.02 |
| Methocel 40-100 (Dow) | 1.50 |
| Glycerine | 3.00 |
| Sodium lauryl sulfate | 15.00 |
| Vitamin A oil | 0.1 |
| Vitamin E oil | 0.01 |

EXAMPLE 6

Cleansing Cream

| INGREDIENTS | AMOUNTS |
| --- | --- |
| 8,8-dipropyl-2-azaspiro[4.5]decane-2-piperidinopropyl dihydrochloride | 5.0% by weight |
| Synthetic beeswax | 14.0 |
| PPG2 Myristyl propionate | 5.0 |
| Lanolin Alcohol | 0.5 |
| Mineral Oil | 36.0 |
| Propyl Paraben | 0.15 |
| Sodium Borate | 1.0 |
| Water | 38.35 |

EXAMPLE 7

Skin Gel

| INGREDIENTS | AMOUNTS |
| --- | --- |
| 8,8-dipropyl-2-azaspiro[4.5]decane-2-piperidinopropyl dihydrochloride | 2.0% by weight |
| PPG2 Myristyl Ether Propionate | 45.0 |
| PPG10 Cetyl Ether | 5.0 |
| C18–C36 Triglyceride | 4.0 |
| Myristyl Myristate | 3.0 |
| Glyceryl Tribebenate | 2.0 |
| Cyclomethicone | 34.0 |
| Polyethylene | 5.0 |

EXAMPLE 8

Skin Lotion

| INGREDIENTS | AMOUNTS |
| --- | --- |
| 8,8-dipropyl-2-azaspiro[4.5]decane-2-piperidinopropyl dihydrochloride | 1.0% by weight |
| DEA Oleth 3 Phosphate | 1.0 |
| Emulsifying Wax | 2.0 |
| C18–C36 Wax Fatty Acids | 1.0 |
| PPG2 Myristyl Propionate | 5.0 |
| Glycerine | 3.0 |
| Triethanolamine | 0.5 |
| Water | 86.5 |

EXAMPLE 9

Shampoo Gel

| INGREDIENTS | AMOUNTS |
|---|---|
| 8,8-dipropyl-2-azaspiro[4.5]decane-2-piperidinopropyl dihydrochloride | 2.0% by weight |
| Isopropanolamine Lauryl Sulfate | 81.5% |
| Cocamide DEA | 8.0 |
| C18–C36 Wax Acid Glyceryl Ester | 4.5 |
| PPG5 Ceteth 10 Phosphate | 4.0 |

EXAMPLE 10

Cream Shampoo

| INGREDIENTS | AMOUNTS |
|---|---|
| 8,8-dipropyl-2-azaspiro[4.5]decane-2-piperidinopropyl | 0.1% by weight |
| Sodium Laureth Sulfate | 65 |
| Glyceryl Tribebenate | 2.0 |
| Hydrolysed Collagen | 1.0 |
| Lauric Diethanolamide | 5.0 |
| Water | 26.9 |

While the above descriptions and examples fully describe the invention and the preferred embodiments thereof, it is understood that the invention is not limited to the particular disclosed embodiments coming within the scope of the following claims.

What is claimed is:

1. A method of treatment of psoriasis in a mammal in need thereof which comprises administering to such mammal an effective amount of a compound of the formula

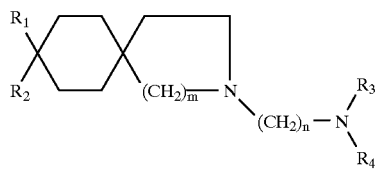

(I)

wherein:

n is 3–7;

m is 1 or 2;

$R^1$ and $R^2$ are the same or different and are selected from hydrogen or straight or branched chain alkyl, provided that the total number of carbon atoms contained by $R^1$ and $R^2$ when taken together is 5–10; or $R^1$ and $R^2$ together form a cyclic alkyl group having 3–7 carbon atoms;

$R^3$ and $R^4$ are the same or different and are selected from hydrogen or straight chain alkyl having 1–3 carbon atoms; or $R^3$ and $R^4$ are joined together with the nitrogen to form a heterocyclic group having 5–8 atoms; or a pharmaceutically acceptable salt or hydrate or solvate thereof.

2. The method of claim 1 wherein the mammal being treated is a human.

3. The method of claim 1 wherein the compound is N,N-dimethyl-8,8-dipropyl-2-azaspiro[4.5]decane-2-propanamine; or a pharmaceutically acceptable salt, hydrate or solvate thereof.

4. The method of claim 1 wherein the compound is 8,8-dipropyl-2-azaspiro[4.5]decane-2-piperidinopropyl; or a pharmaceutically acceptable salt, hydrate or solvate thereof.

5. The method of claim 1 wherein the compound is administered orally.

6. The method of claim 5 wherein from about 0.01 mg/kg to about 10 mg/kg of compound is administered per day.

7. The method of claim 1 wherein the compound is administered parenterally.

8. The method of claim 7 wherein from about 0.01 mg/kg to about 10 mg/kg of compound is administered per day.

9. The method of claim 1 wherein the compound is administered topically.

10. The method of claim 9 wherein from about 0.01 mg/kg to about 10 mg/kg of compound is administered per day.

* * * * *